(12) United States Patent
Gulaka et al.

(10) Patent No.: US 10,185,805 B2
(45) Date of Patent: Jan. 22, 2019

(54) MEDICAL IMAGE PROCESSING APPARATUS AND METHOD

(71) Applicant: SAMSUNG ELECTRONICS CO., LTD., Suwon-si (KR)

(72) Inventors: Praveen Gulaka, Suwon-si (KR); Hyun-hee Jo, Osan-si (KR); Se-Jin Yoo, Anseong-si (KR); Jae-moon Jo, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 441 days.

(21) Appl. No.: 14/791,564

(22) Filed: Jul. 6, 2015

(65) Prior Publication Data
US 2016/0026761 A1    Jan. 28, 2016

(30) Foreign Application Priority Data

Jul. 22, 2014    (KR) .................. 10-2014-0092661

(51) Int. Cl.
*G06F 19/00* (2018.01)
*G06F 3/0481* (2013.01)
*G06F 3/0482* (2013.01)
*G06F 3/0484* (2013.01)

(52) U.S. Cl.
CPC .......... *G06F 19/321* (2013.01); *G06F 3/0482* (2013.01); *G06F 3/04817* (2013.01); *G06F 3/04842* (2013.01); *G06F 3/04845* (2013.01)

(58) Field of Classification Search
CPC .. G06F 19/321; G06F 3/0482; G06F 3/04845; G06F 19/00; G06F 19/30; G06T 7/0012
See application file for complete search history.

(56) References Cited

U.S. PATENT DOCUMENTS

| | | | |
|---|---|---|---|
| 6,904,161 | B1 | 6/2005 | Becker et al. |
| 7,604,601 | B2 | 10/2009 | Altmann et al. |
| 7,962,348 | B2 | 6/2011 | Dew et al. |
| 8,370,293 | B2 | 2/2013 | Iwase et al. |

(Continued)

FOREIGN PATENT DOCUMENTS

| | | |
|---|---|---|
| JP | 7-253870 A | 10/1995 |
| JP | 2005-080969 A | 3/2005 |

(Continued)

OTHER PUBLICATIONS

Communication dated May 27, 2015 issued by Korean Intellectual Property Office in counterpart Korean Application No. 10-2014-0092661.

*Primary Examiner* — Jeffrey A Gaffin
*Assistant Examiner* — Bille M Dahir
(74) *Attorney, Agent, or Firm* — Sughrue Mion, PLLC

(57) ABSTRACT

A medical image processing apparatus and method are provided. The medical image processing apparatus includes a controller configured to acquire an icon based on information in a medical image file of an object, the icon having a shape of the object and comprising one or more sub-icons, and a display configured to display the icon. Each of the one or more sub-icons corresponds to an anatomical region of the object is configured to accept input to perform one or more image processing functions associated with the corresponding anatomical region.

25 Claims, 8 Drawing Sheets

(56) References Cited

U.S. PATENT DOCUMENTS

| | | | |
|---|---|---|---|
| 2010/0023857 A1* | 1/2010 | Mahesh | G06F 3/016 715/701 |
| 2010/0053214 A1* | 3/2010 | Goto | A61B 6/04 345/629 |
| 2011/0028825 A1 | 2/2011 | Douglas et al. | |
| 2013/0174077 A1 | 7/2013 | Asami et al. | |
| 2014/0055456 A1 | 2/2014 | Holthuizen et al. | |
| 2014/0071072 A1 | 3/2014 | Itai | |
| 2015/0363053 A1* | 12/2015 | Aoyama | G06F 3/0482 715/838 |

FOREIGN PATENT DOCUMENTS

| | | | |
|---|---|---|---|
| JP | 2007-330374 A | 12/2007 | |
| JP | 2014-54358 A | 3/2014 | |
| KR | 10-2006-0112244 A | 10/2006 | |
| KR | 10-2010-0096224 A | 9/2010 | |

* cited by examiner

FIG. 5

| EXAMPLE | ICON | SELECTION OPERATION | FUNCTION | ICON | SELECTION OPERATION | FUNCTION | EXAMPLE |
|---|---|---|---|---|---|---|---|
| 1 |  | Drag | Show all contours |  | L-Click | Select LV endo-contour | 9 |
| 2 |  | L-Click | Hide all contours |  | L-Click | Select LV epi-contour | 10 |
| 3 | 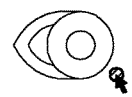 | R-Click | Hide LV endo-contour |  | L-double Click | Select RV endo- and epi-contours | 11 |
| 4 |  | R-Click | Hide LV epi-contour |  | L-Click | Select RV endo-contour | 12 |
| 5 |  | R-double Click | Hide LV endo- and epi-contours |  | L-Click | Select RV epi-contour | 13 |
| 6 |  | R-Click | Hide RV endo-contour |  | L-double Click | Select RV endo- and epi-contours | 14 |
| 7 |  | R-Click | Hide RV epi-contour | | | | |
| 8 |  | R-double Click | Hide RV endo- and epi-contours | | | | |

Drawing LV endo-contour
Drawing LV epi-contour
Drawing RV endo-contour
Drawing RV epi-contour Correct endo-contour
Correct epi-contour
Click-draw-mode Automatic LV contour detection
Propagate LV contour for current phase
Propagate LV contour for entire stack
Automatic RV contour detection (only endo-contour)
Papillary muscle include/exclude

MEDICAL IMAGE PROCESSING APPARATUS AND METHOD

RELATED APPLICATION

This application claims priority from Korean Patent Application No. 10-2014-0092661, filed on Jul. 22, 2014, in the Korean Intellectual Property Office, the disclosure of which is incorporated herein in its entirety by reference.

BACKGROUND

1. Field

Apparatuses and methods consistent with exemplary embodiments relate to a medical image processing apparatus and method, and more particularly, to a medical image processing apparatus and method that provide an intuitive icon for processing a medical image.

2. Description of the Related Art

Medical image data may be acquired by an X-ray apparatus, a computed tomography (CT) apparatus, a magnetic resonance imaging (MRI) apparatus, an ultrasound apparatus, and various medical image systems. Various image processing functions may be performed on the acquired medical image data, including functions for determining or analyzing a state of an object to identify conditions such as diseases.

An image processing function may be determined based on a medical image data acquisition modality, an anatomy of an object, and an image protocol. The medical image data acquisition modality may include an X-ray apparatus, a CT apparatus, an MRI apparatus, or an ultrasound apparatus. The anatomy of the object may include a heart, a brain, and a spine. The image protocol may include a perfusion study, volume measurement, and calcification measurement.

As described above, there are various image processing functions. Therefore, when icons for executing various image processing functions are displayed in the medical image processing apparatus, too many icons may be displayed. When there are too many icons displayed on a screen, it is difficult for a user to find an icon for executing a desired image processing function. Thus, operating the medical image processing apparatus becomes cumbersome and a user's experience deteriorates.

SUMMARY

One or more exemplary embodiments provide a medical image processing apparatus and method that display an intuitive icon for processing a medical image.

According to an aspect of an exemplary embodiment, there is provided a medical image processing apparatus including a controller configured to acquire an icon based on information in a medical image file of an object, the icon having a shape of the object and comprising one or more sub-icons; and a display configured to display the icon, wherein each of the one or more sub-icons corresponds to an anatomical region of the object and is configured to accept input to perform one or more image processing functions associated with a corresponding anatomical region.

In response to one sub-icon from among the one or more sub-icons being selected by a user, the controller may control the display to display a shortcut menu that provides the one or more image processing functions corresponding to the selected sub-icon.

In response to one image processing function from among the one or more image processing functions displayed in the shortcut menu being selected by the user, the controller may perform image processing by using the selected image processing function on the medical image file.

The one or more image processing functions displayed in the shortcut menu may be selected by the user or selected according to a frequency of use.

Each of a plurality of selection operations may correspond to the one or more image processing functions, and in response to one sub-icon being selected from among the one or more sub-icons through one of the plurality of selection operations by a user, the controller may perform image processing on the medical image file by using an image processing function corresponding to the one selection operation.

A correspondence relationship between the plurality of selection operations and the one or more image processing functions is selected by the user.

In response to one sub-icon being selected through a selection operation by the user, the controller may control to change a state of the selected sub-icon displayed on the display.

The controller may control to change the state of the selected sub-icon based on the image processing function corresponding to the selection operation.

The medical image processing apparatus may further include an input device that is configured to receive a selection operation from a user, wherein, based on the selection operation, one sub-icon is selected from among the one or more sub-icons, and one image processing function is selected from among the one or more image processing functions.

The control unit may acquire the icon and determine the one or more image processing functions based on information about the object included in a header of the medical image file.

According to an aspect of another exemplary embodiment, there is provided a medical image processing method including: acquiring an icon based on information in a medical image file of an object, the icon having a shape of the object and comprising one or more sub-icons; and displaying the icon, wherein each of the one or more sub-icons corresponds to an anatomical region of the object and is configured to accept input to perform one or more image processing functions associated with a corresponding anatomical region.

The medical image processing method may further include, in response to one sub-icon from among the one or more sub-icons being selected by a user, displaying a shortcut menu that provides the one or more image processing functions corresponding to the selected sub-icon.

The medical image processing method may further include, in response to one image processing function from among the one or more image processing functions displayed in the shortcut menu being selected by the user, performing image processing by using the selected image processing function.

The one or more image processing functions displayed in the shortcut menu may be selected by the user or selected according to a frequency of use.

A plurality of selection operations may correspond to the one or more image processing functions, and the medical image processing method may further include in response to one sub-icon being selected by a user from among the one or more sub-icons through one of the plurality of selection operations, performing image processing on the medical image file by using an image processing function corresponding to the one selection operation.

A correspondence relationship between the plurality of selection operations and the one or more image processing functions may be selected by the user.

When one sub-icon is selected through a selection operation by the user, a state of the selected sub-icon may be changed.

The changing of the state of the selected sub-icon may be based on an image processing function corresponding to the selection operation.

The medical image processing method may further include receiving a selection operation from a user, and response to the selection operation, one sub-icon may be selected from among the one or more sub-icons, and one image processing function may be selected from among the one or more image processing functions.

BRIEF DESCRIPTION OF THE DRAWINGS

These and/or other aspects will become apparent and more readily appreciated from the following description of the exemplary embodiments, taken in conjunction with the accompanying drawings in which:

FIG. 5 illustrates an example of an image processing function which is executed according to a sub-icon selecting scheme;

DETAILED DESCRIPTION OF EXEMPLARY EMBODIMENTS

Figure 1:
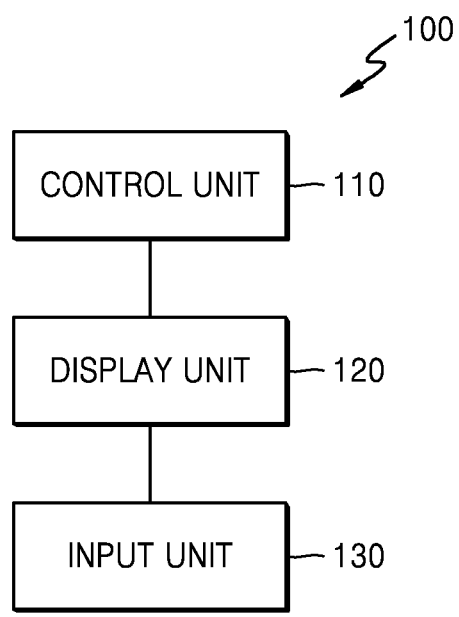
FIG. 1 illustrates a medical image processing apparatus according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description.

The advantages, features and aspects of the inventive concept will become apparent from the following description of the embodiments with reference to the accompanying drawings, which is set forth hereinafter. The inventive concept may, however, be embodied in different forms and should not be construed as limited to the exemplary embodiments set forth herein. Rather, these exemplary embodiments are provided so that this disclosure will be thorough and complete, and will fully convey the scope of the inventive concept to those of ordinary skill in the art.

Terms used herein will be briefly described, and the inventive concept will be described in detail.

Terms used in the inventive concept have been selected as general terms which are widely used at present, in consideration of the functions of the inventive concept, but may be altered according to the intent of an operator of ordinary skill in the art, conventional practice, or introduction of new technology. If there is a term which is arbitrarily selected by the applicant in a specific case, in which case a meaning of the term will be described in detail in a corresponding description portion of the inventive concept. Therefore, the terms should be construed on the basis of the entire content of this specification instead of a simple name of each of the terms.

In this disclosure below, when it is described that an element comprises (or includes or has) one or more elements, it should be understood that it may comprise (or include or has) only those elements, or it may comprise (or include or have) other elements as well as those elements if there is no specific limitation. The term "module" (i.e. unit), as used herein, means, but is not limited to, a software or hardware component, such as a Field Programmable Gate Array (FPGA) or an Application Specific Integrated Circuit (ASIC), which performs certain tasks. A module may advantageously be configured to reside in the addressable storage medium and configured to execute on one or more processors. Thus, a module may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables. The functionality provided for in the components and modules may be combined into fewer components and modules or further separated into additional components and modules.

Exemplary embodiments of the inventive concept capable of being implemented by those of ordinary skill in the art will now be described in detail with reference to the accompanying drawings. In the accompanying drawings, a portion irrelevant to a description of the inventive concept will be omitted for clarity.

The term "image" used herein may denote multi-dimensional data composed of discrete image factors (for example, pixels in a two-dimensional (2D) image and pixels in a three-dimensional (3D) image). For example, an image may include a medical image of an object which is acquired by an X-ray apparatus, a CT apparatus, a magnetic resonance imaging (MRI) apparatus, an ultrasound apparatus, or another medical image photographing apparatus.

Moreover, the term "object" used herein may include a person, an animal, a part of the person, or a part of the animal. For example, an object may include an organ such as a liver, a heart, a womb, a brain, breasts, an abdomen, or the like, or a blood vessel. The term "object" may include a phantom. The phantom denotes a material having a volume very close to a density of organisms and an effective atomic number, and may include a spherical phantom having a temper similar to a human body. The term "object" used herein may also include any object that may be imaged by the imaging apparatuses disclosed herein.

Moreover, the term "user" used herein may be a medical expert, and may be a doctor, a nurse, a medical technologist, a medical image expert, or the like, or may be an engineer repairing a medical apparatus. However, the user is not limited thereto. The user may an operator of an image processing apparatus.

FIG. 1 illustrates a medical image processing apparatus 100 according to an exemplary embodiment.

Referring to FIG. 1, the medical image processing apparatus 100 includes a control unit 110 (e.g., a controller, processor, etc.) and a display unit 120 (e.g., a display, etc.). The control unit 110 acquires an icon having a shape of an object, based on a medical image file about the object. The medical image file may include information, indicating what type of object type is pictured in the medical image, and information indicating the view the shape of the object is shown in the medical image. For example, a type of an object may be a heart, a brain, and a knee joint, and a view may be a sagittal plane, a coronal plane, and an axial plane. Pieces of information about the object may be included in a header of the medical image file.

The control unit 110 may identify a type of an object, based on the header of the medical image file. Therefore, the control unit 110 may acquire or generate an icon having the shape of the object depending on the identified type of the object. For example, when the type of the object is a heart, the control unit 110 may acquire an icon having a heart shape, and when the type of the object is a brain, the control unit 110 may acquire an icon having a brain shape. The control unit 110 may also identify a view of the object, based on the header of the medical image file. In this case, the control unit 110 may acquire or generate an icon having the shape of the object corresponding to the view of the object, based on the type of the object and the view of the object. An icon corresponding to each view of the object based on the type of the object may be stored in the medical image processing apparatus 100. Therefore, the control unit 110 may select or generate a corresponding icon depending on identified object information in the medical image file.

The display unit 120 displays the icon acquired by the control unit 110. The icon includes at least one sub-icon. The at least one sub-icon corresponds to an anatomical region of each object and corresponds to at least one image processing function associated with a corresponding anatomical region.

The medical image file may include the header and medical image data. The header may include information about the medical image file, and the medical image data may include a medical image of an object. Information (included in the header) about the medical image file may include type information of the object and medical image data acquisition modality information. For example, the type of the object may include a heart, a knee joint, a spine, and a brain such as an anatomy of the object, but is not limited thereto. The medical image data acquisition modality may include a type of apparatus, such as an X-ray apparatus, a CT apparatus, an MRI apparatus, or an ultrasound apparatus, but is not limited thereto. In addition, the header may further include date that the image was taken and personal information of a patient. The medical image file may be a file that is based on the digital imaging and communications in medicine (DICOM) standard.

Moreover, the control unit 110 may determine at least one image processing function, based on the identified type of the object. The control unit 110 may also make each of sub-icons included in an icon correspond to at least one image processing function.

The medical image processing apparatus 100 may further include an input unit 130 (i.e., input device). A user may input a selection operation of the user through the input unit 130. Based on the selection operation of the user, one sub-icon may be selected from among at least one or more sub-icons, and one image processing function may be selected from among at least one or more image processing functions. The input unit 130 may include a keyboard, a mouse, a trackball, a voice recognition unit, a gesture recognition unit, a touch screen, and a stylus pen, and include input devices.

The control unit 110 may perform image processing on the medical image file according to an image processing function corresponding to the selection operation of the user.

The display unit 120 may display medical image data and a result of the image processing of the medical image file, in addition to an icon. The display unit 120 may display information, which is necessary for a user to manipulate the medical image processing apparatus 100, such as a user interface (UI), user information, or object information. The display unit 120 may include a CRT display, an LCD, a PDP, an OLED display, a FED, an LED display, a VFD, a DLP display, a PFD, a 3D display, a transparent display, etc., and include various other display devices.

Although not shown in FIG. 1, the medical image processing apparatus 100 may further include a communication unit such as a transceiver, etc. and a storage unit such as a memory, etc.

The communication unit is wired to a network or wirelessly connected to a network and communicates with an external device or a server. The communication unit may exchange data with a hospital server or another medical device in a hospital that is connected with a picture archiving and communications system (PACS). Furthermore, the communication unit may perform data communication according to the digital imaging and communications in medicine (DICOM) standard.

The storage unit may store a medical image file. When the medical image file stored in the storage unit is executed by a user, the medical image processing apparatus 100 may display an icon in the display unit 120. Therefore, the user may intuitively instruct execution through the input unit 130 so that a desired image processing function is performed on the medical image file by using the icon.

Hereinafter, when the control unit 110 identifies a type of an object as a heart on the basis of a medical image file, an operation of the medical image processing apparatus 100 will be described.

Figure 2A:
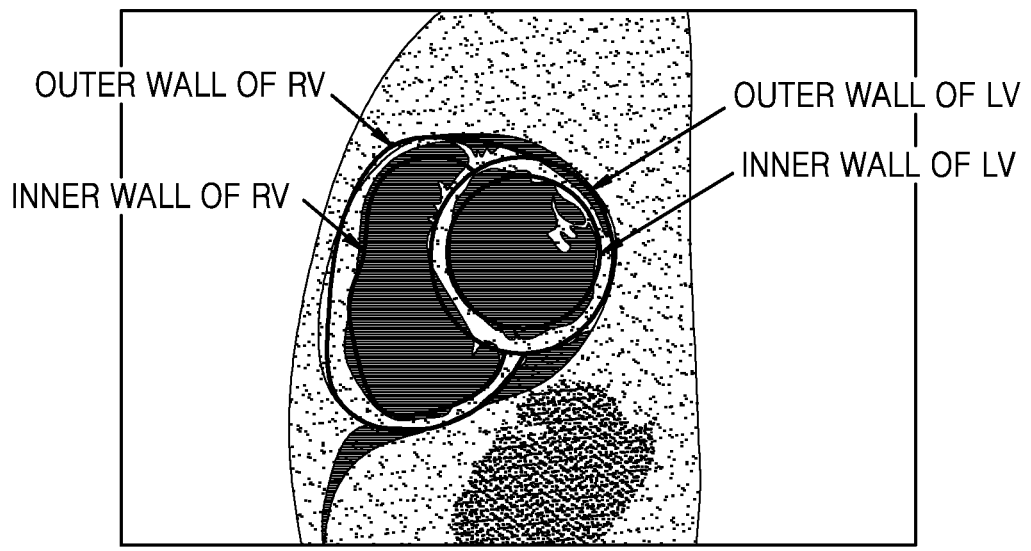
FIGS. 2A and 2B illustrate an icon according to an exemplary embodiment.
Figure 2B:
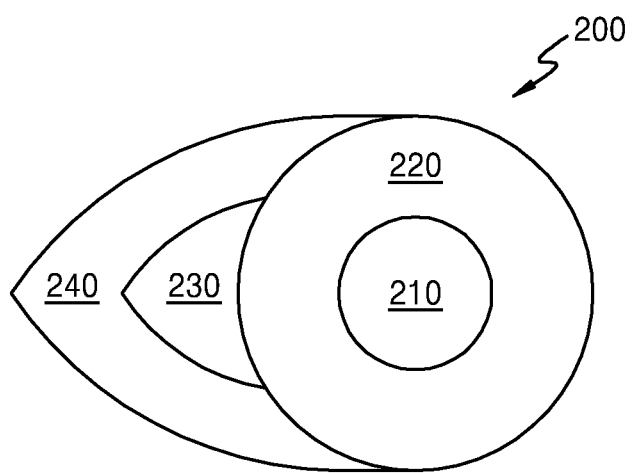

FIGS. 2A and 2B illustrate an icon according to an exemplary embodiment.

Referring to FIG. 2A, when an object is a heart, the heart may include anatomical regions such as an inner wall and an outer wall of a left ventricle (LV) and an inner wall and an outer wall of a right ventricle (RV).

Referring to FIG. 2B, an icon 200 has a shape of a heart. The icon 200 may include at least one or more sub-icons 210, 220, 230 and 240. A first sub-icon 210 corresponds to an inner wall of an LV which is an anatomical region of the heart. A second sub-icon 220 corresponds to an outer wall of the LV, a third sub-icon 230 corresponds to an inner wall of an RV, and a fourth sub-icon 240 corresponds to an outer wall of the RV. That is, the sub-icons 210, 220, 230 and 240 correspond to anatomical regions of the object, respectively.

In an exemplary embodiment, an icon is acquired in a shape of an object, and a sub-icon included in the icon corresponds to an anatomical region of the object. Therefore, a user may intuitively recognize the object corresponding to the icon and may intuitively recognize the anatomical region of the object corresponding to the sub-icon.

FIG. 2 is merely an example of an icon when an object is a heart, and the present embodiment is not limited thereto. Although not shown in FIG. 2, an icon may further include a sub-icon corresponding to a papillary muscle that is an anatomical region of a heart.

When an object is a heart, image processing functions may include selection, segmentation, propagation, contour show/hide, and contour correction of each ventricle. Each sub-icon may show or reflect a corresponding image processing function performed on the corresponding anatomical region.

Figure 3:
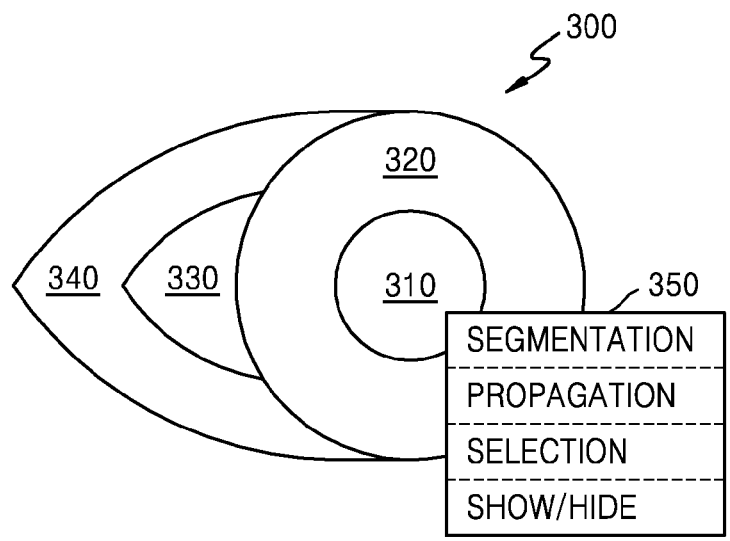
FIG. 3 illustrates image processing functions corresponding to a sub-icon according to an exemplary embodiment.

FIG. 3 illustrates image processing functions corresponding to a sub-icon according to an exemplary embodiment. An icon 300 of FIG. 3 corresponds to the icon 200 of FIG. 2, and thus, a repetitive description is omitted.

Referring to FIG. 3, when a sub-icon 310 is selected by a user, a shortcut menu 350 that provides at least one image processing function corresponding to the selected sub-icon 310 is displayed. The shortcut menu 350 provides functions such as segmentation, propagation, selection, and contour show/hide. The user may select a desired image processing function from among a plurality of image processing functions which are provided through the shortcut menu 350. For example, the segmentation of the shortcut menu 350 may be selected by the user. Then, the medical image processing apparatus 100 (see FIG. 1) performs image processing on a medical image file for segmenting an inner wall of an LV corresponding to the sub-icon 310. The sub-icon 310 may be updated to reflect the image processing on a medical image file for segmenting an inner wall of an LV corresponding to the sub-icon 310

As another example, when the user desires to perform image processing on the medical image file for propagating an outer wall of an RV, the user may select a sub-icon 340 corresponding to the outer wall of the RV. When the sub-icon 340 is selected, a shortcut menu corresponding to the sub-icon 340 is displayed. When propagation provided through the shortcut menu is selected, the image processing (desired by the user) for propagating the outer wall of the RV is performed on the medical image file. The sub-icon 340 may be updated to reflect the image processing (desired by the user) for propagating the outer wall of the RV that is performed on the medical image file.

According to an exemplary embodiment, the user may intuitively recognize an anatomical region of an object corresponding to a sub-icon. Therefore, the user intuitively, easily, quickly selects a sub-icon corresponding to a desired anatomical region of an object for which image processing is to be performed. When a sub-icon is selected, a shortcut menu providing a plurality of image processing functions relevant to a corresponding anatomical region may be provided. Therefore, the user easily, conveniently selects a desired image processing function from the shortcut menu. Accordingly, convenience is provided to a user using the medical image processing apparatus 100.

Referring again to FIG. 3, at least one image processing function included in the shortcut menu 350 may be variously determined. A shortcut menu 350 set as a default may include all or some image processing functions associated with a corresponding sub-icon 310.

The image processing functions included in the shortcut menu 350 may be adjusted by the user. That is, the image processing functions may be customized based on a preference of the user. For example, the image processing functions included in the shortcut menu 350 may be changed based on the user's selection. Alternatively, the image processing functions included in the shortcut menu 350 may be adjusted based on a frequency of use by the user. For example, when an arbitrary image processing function is used more than the predetermined number of times, the arbitrary image processing function may be added to the shortcut menu 350. On the other hand, when an arbitrary image processing function is used less than the predetermined number of times for a certain time, the arbitrary image processing function may be removed from the shortcut menu 350.

Moreover, in FIG. 3, the functions included in the shortcut menu 350 are displayed in a text type, but this is merely an example. The functions included in the shortcut menu 350 may be expressed in a picture type or a combination type of a text and a picture, which is intuitively recognized by the user.

In FIG. 3, the first sub-icon 310 is selected, but this is merely an example. The other sub-icons 320 to 340 may also be selected. A scheme of selecting the sub-icons 310 to 340 desired by the user may be various depending on the input unit 130 (see FIG. 1). For example, when the input unit 130 (see FIG. 1) is a mouse, the user clicks or double-clicks a sub-icon which is to be selected, thereby selecting the sub-icon. Alternatively, when the input unit 130 (see FIG. 1) is a touch screen, the user touches one of the sub-icons 310 to 340 displayed on the touch screen, thereby selecting the touched sub-icon. There are various selection methods such as long tap, drag, left/right click, and left/right double click, in addition to click, double-click, and touch.

Figure 4:
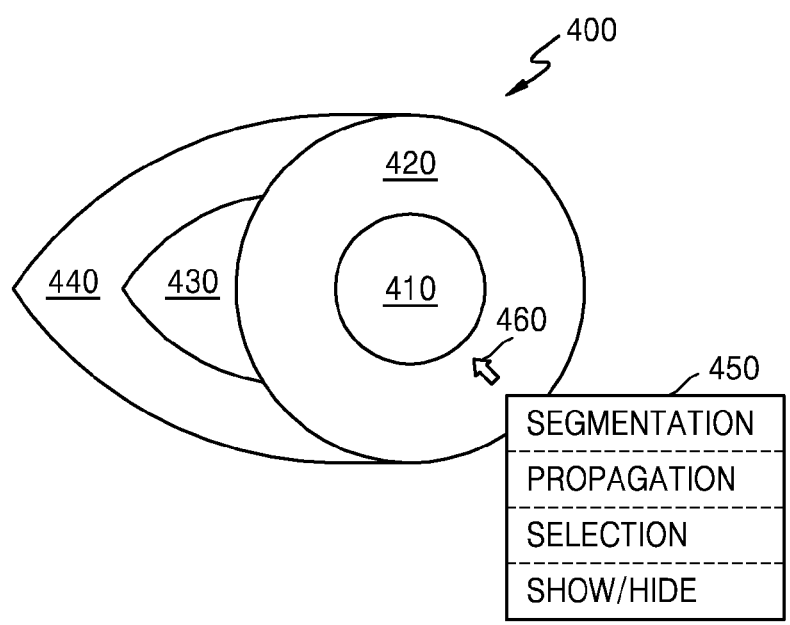
FIG. 4 illustrates a sub-icon selecting scheme.

FIG. 4 illustrates a sub-icon selecting scheme. An icon 400 of FIG. 4 corresponds to the icon 200 of FIG. 2, and thus, a repetitive description is omitted.

Referring to FIG. 4, when a pointer 460 is simply located on a second sub-icon 420, the second sub-icon 420 may be an icon selected by a user. The pointer 460 may be displayed on a screen of the display unit 120 and may be moved by the user in the screen. When the pointer 460 is located on the second sub-icon 420 which is to be selected by the user, a shortcut menu 450 may be displayed. In FIG. 4, the pointer 460 may be displayed in an arrow shape or may be displayed in another shape such as a cursor.

In FIGS. 3 and 4, when the sub-icon 310 (420) is selected by the user, the shortcut menu 350 (450) corresponding to the sub-icon 310 (420) is provided. When one of the image processing functions such as segmentation, propagation, selection, and show/hide is selected from the shortcut menu 350 (450), the selected image processing function may be performed.

As described above with reference to FIGS. 3 and 4, the user may select a sub-icon in various methods. Therefore, the above-described sub-icon selecting schemes are merely examples, and a sub-icon selecting scheme is not limited to the examples.

Hereinafter, in some exemplary embodiments, a method of performing a corresponding image processing function according to a sub-icon selecting scheme will be described.

FIG. 5 illustrates an example of an image processing function which is executed according to a sub-icon selecting scheme. The First to fourteenth examples of a table shown in FIG. 5 will be described in order.

In the first example, when an icon including four sub-icons is selected by a drag scheme, an image processing function of showing all contours (show all contours) may be performed.

In the second example, when a part which is not an icon is selected by a left-click (L-click) scheme, an image processing function of hiding all contours (hide all contours) may be performed.

In the third example, when a sub-icon corresponding to an inner wall of an LV is selected by a right-click (R-click) scheme, an image processing function of hiding an LV endo-contour (hide LV endo-contour) may be performed.

In the fourth example, when a sub-icon corresponding to an outer wall of the LV is selected by the R-click scheme, an image processing function of hiding an LV epi-contour (hide LV epi-contour) may be performed.

In the fifth example, when a sub-icon corresponding to the inner wall of the LV or a sub-icon corresponding to the outer wall of the LV is selected by a right-double (R-double) click scheme, an image processing function of hiding the LV endo-contour and the LV epi-contour (hide LV endo- and epi-contours) may be performed.

In the sixth example, when a sub-icon corresponding to an inner wall of an RV is selected by the R-click scheme, an image processing function of hiding an RV endo-contour (hide RV endo-contour) may be performed.

In the seventh example, when a sub-icon corresponding to an outer wall of the RV is selected by the R-click scheme, an image processing function of hiding an RV epi-contour (hide RV epi-contour) may be performed.

In the eighth example, when a sub-icon corresponding to the inner wall of the RV or a sub-icon corresponding to the outer wall of the RV is selected by the R-double click scheme, an image processing function of hiding the RV endo-contour and the RV epi-contour (hide RV endo- and epi-contours) may be performed.

In the ninth example, when a sub-icon corresponding to the inner wall of the LV is selected by a left-click (L-click) scheme, an image processing function of selecting the LV endo-contour (select LV endo-contour) may be performed.

In the tenth example, when a sub-icon corresponding to the outer wall of the LV is selected by the L-click scheme, an image processing function of selecting the LV epi-contour (select LV epi-contour) may be performed.

In the eleventh example, when a sub-icon corresponding to the inner wall of the LV or a sub-icon corresponding to the outer wall of the LV is selected by a left-double (L-double) click scheme, an image processing function of selecting the LV endo-contour and the LV epi-contour (select LV endo- and epi-contours) may be performed.

In the twelfth example, when a sub-icon corresponding to the inner wall of the RV is selected by the L-click scheme, an image processing function of selecting the RV endo-contour (select RV endo-contour) may be performed.

In the thirteenth example, when a sub-icon corresponding to the outer wall of the RV is selected by the L-click scheme, an image processing function of selecting the RV epi-contour (select RV epi-contour) may be performed.

In the fourteenth example, when a sub-icon corresponding to the inner wall of the RV or a sub-icon corresponding to the outer wall of the RV is selected by the L-double click scheme, an image processing function of selecting the RV endo-contour and the RV epi-contour (select RV endo- and epi-contours) may be performed.

As described above, a corresponding image processing function such as selection of an LV epi-contour may be performed according to a sub-icon selecting scheme such as the L-click scheme or the L-double click scheme. That is, an image processing function corresponding to an icon or a sub-icon may be performed according to a scheme of selecting an icon or a sub-icon. FIG. 5 is merely an example, and some exemplary embodiments are not limited thereto.

A relationship between a sub-icon selecting scheme and a corresponding image processing function may be fixed as shown in FIG. 5. In this case, as a use experience of a user increases, convenience for use increases.

Alternatively, a sub-icon selecting scheme and a corresponding image processing function may be customized according to a preference of a user. In this case, a convenience of the user increases. In particular, the drag and double click may be performed by using a mouse input, touch screen input, or other input device.

Furthermore, a state of a sub-icon may be changed according to an icon or sub-icon selecting scheme like a color, a line, and a sharpness of a sub-icon being changed. In this case, by correlating a changed state of a sub-icon and a corresponding image processing function, the user may intuitively allow an image processing function to be performed through an icon.

Figure 6:
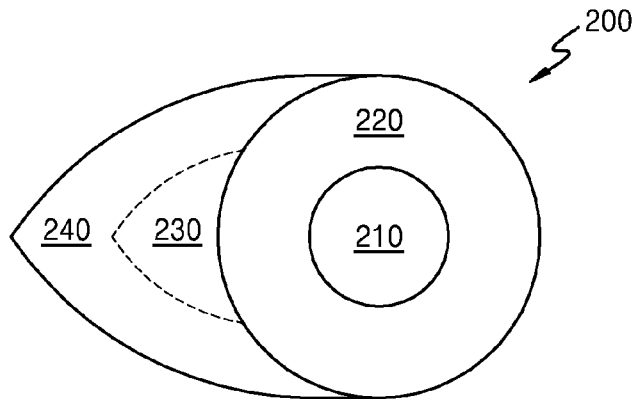
FIGS. 6, 7 and 8 illustrate examples of a state of a changed sub-icon.
Figure 7:
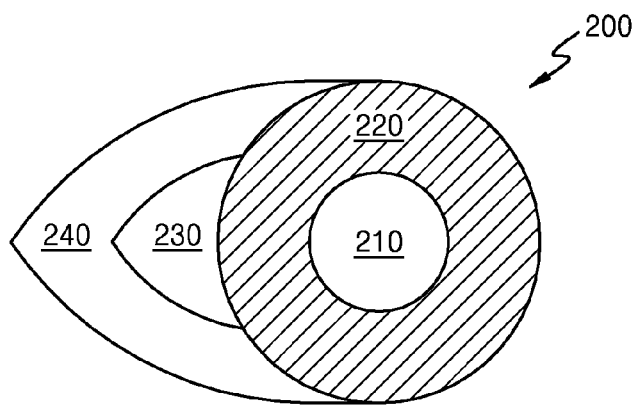
Figure 8:
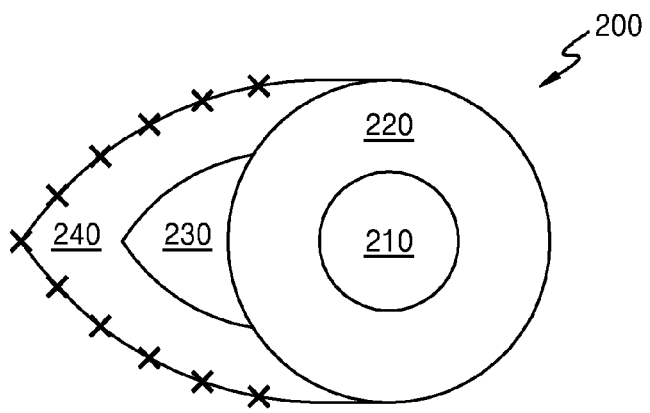

FIGS. 6 to 8 illustrate examples of a state of a changed sub-icon. FIGS. 6 to 8 illustrate a case which is changed in the icon of FIG. 2. Therefore, details described above with reference to FIG. 2 are not described.

Referring to FIG. 6, a line composing a sub-icon 230 of an icon 200 corresponding to an inner wall of an RV is changed to a dot line. For example, when the sub-icon 230 is selected by the R-click scheme, the sub-icon 230 may be changed as illustrated in FIG. 6. A scheme of selecting the sub-icon 230 in which the line composing the sub-icon 230 is changed to a dot line may correspond to an image processing function of hiding an RV endo-contour. Alternatively, the changing of the sub-icon 230 illustrated in FIG. 6 may correspond to an image processing function of correcting the RV endo-contour.

Referring to FIG. 7, a color of a sub-icon 220 of the icon 200 corresponding to an outer wall of an LV may be changed. For example, an achromatic color may be changed to a chromatic color, or a chromatic color may be changed to an achromatic color. For example, when the sub-icon 220 is selected by the R-click scheme, the sub-icon 220 may be changed as illustrated in FIG. 7. A scheme of selecting the sub-icon 220 in which the color of the sub-icon 220 is changed may correspond to an image processing function of selecting or segmenting the outer wall of the LV.

Referring to FIG. 8, X's may be marked on a line composing a sub-icon 240 of an icon 200 corresponding to an outer wall of an RV. For example, when the sub-icon 240 is selected by the double click scheme, the sub-icon 240 may be changed as illustrated in FIG. 8. A scheme of selecting the sub-icon 240 in which X's are marked on the line composing the sub-icon 240 may correspond to an image processing function of correcting a result of segmentation of the outer wall of the RV.

As illustrated in FIGS. 6 to 8, a sub-icon selecting scheme may be associated with the changing of a state, color, shape, line of a sub-icon. The changing of the state of the sub-icon may be associated with a corresponding image processing function. Therefore, when a user performs an image processing function through an icon, a more intuitive interface is provided.

The sub-icon selecting scheme, sub-icon state changing scheme, and image processing function of FIGS. 6 to 8 are merely examples. As another example, when the user selects a sub-icon by using a drag scheme or input, a sharpness of the sub-icon is reduced, and the sub-icon selecting scheme may correspond to an image processing function of correcting a motion for an anatomical region corresponding to the sub-icon. In order for the user to intuitively recognize an image processing function corresponding to a sub-icon selecting scheme, a state of the sub-icon may be variously changed.

Thus far, a case in which an object is a heart has been described. However, the present exemplary embodiment may be applied to a case in which an object is not a heart.

Figure 9A:
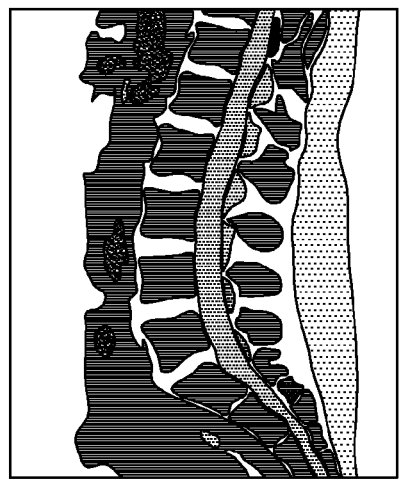
FIGS. 9A and 9B illustrate an icon when an object is a lumbar spine.
Figure 9B:
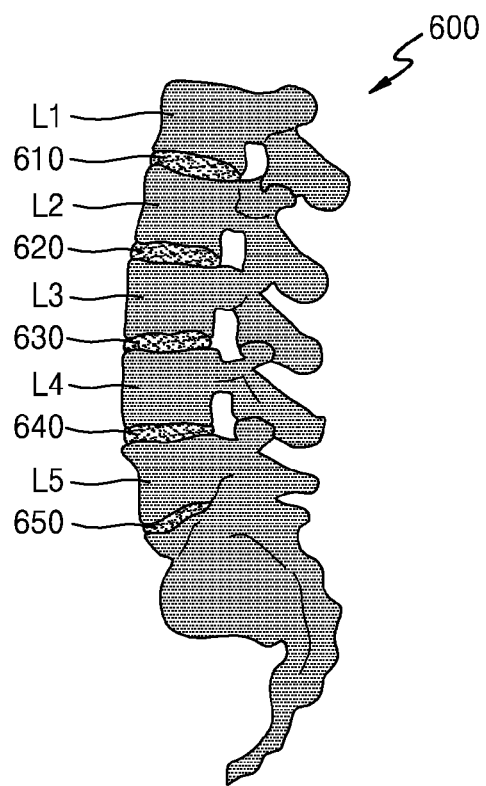

FIGS. 9A and 9B illustrate an icon when an object is a lumbar spine.

Referring to FIG. 9B, an icon 600 is acquired in a shape of a lumbar spine that is an object. The icon 600 includes a plurality of sub-icons L1 to L5 and 610 to 650. The sub-icons L1 to L5 respectively correspond to five lumbar vertebras that are anatomical regions of an object shown in FIG. 9A, and the sub-icons 610 to 650 respectively correspond to lumbar discs between the lumbar vertebras.

When a type of the object is a lumbar spine, image processing functions include lumbar disc segmentation, thickness measurement of lumbar disc that is an interval between lumbar vertebras, and numbering of a lumbar vertebra. For example, when a sub-icon 630 is selected by a user, an image processing function of measuring a thickness of corresponding lumbar disc may be performed. As described above, at least one image processing function may correspond to each the sub-icons L1 to L5 and 610 to 650. A method of performing an image processing function may also be varied according to a shortcut menu providing scheme and a sub-icon selecting scheme.

Figure 10A:
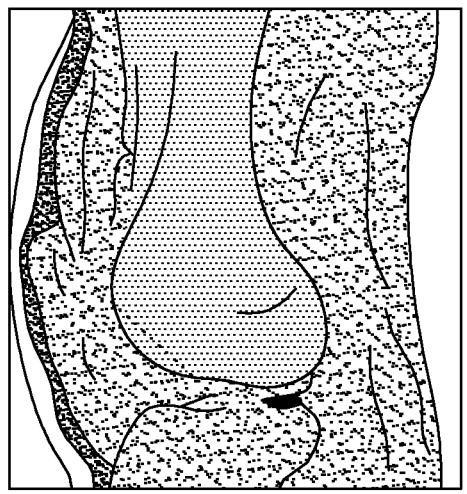
FIGS. 10A and 10B illustrate an icon when an object is a knee joint.
Figure 10B:
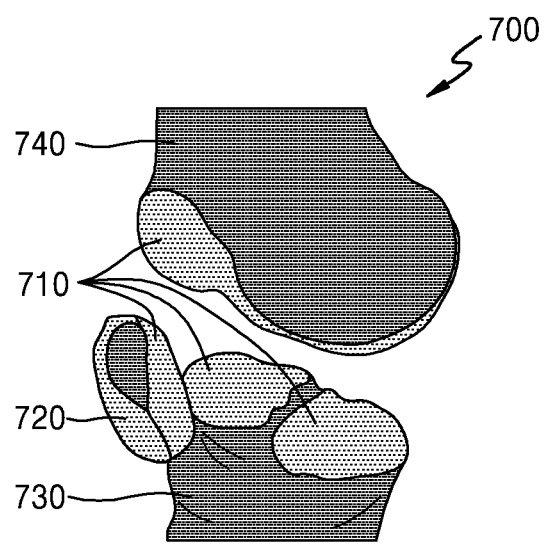

FIGS. 10A and 10B illustrate an icon when an object is a knee joint.

Referring to FIG. 10B, an icon 700 is acquired in a shape of a knee joint that is an object. The icon 700 includes a plurality of sub-icons 710 to 740. A first sub-icon 710 corresponds to a cartilage that is an anatomical region of the object in FIG. 10A, a second sub-icon 720 corresponds to a patella, a third sub-icon 730 corresponds to a tibia, and a fourth sub-icon 740 corresponds to a femur. When a type of the object is a knee joint, image processing functions include cartilage selection, segmentation, and volume or thickness measurement of a cartilage. For example, when the first sub-icon 710 is selected by a user, an image processing function of measuring a thickness of a patella.

Hereinafter, types of other objects will be described.

When a type of an object is a blood vessel, image processing functions include maximal intensity projection (MIP), separation of an artery and a vein, and selection of the artery and the vein. An icon is acquired in a shape of the blood vessel. The icon may include a sub-icon corresponding to the artery and a sub-icon corresponding to the vein.

When a type of an object is a brain of a cerebral infarction patient, image processing functions include segmentation of a core and a penumbra of cerebral infarction, selection of the core and the penumbra, generation of a mismatch map that is a comparison image of a diffusion-weighted image (DWI) and a perfusion-weighted image (PWI), and calculation of region of interest (ROI) statistics. An icon may be generated in a brain shape and may include sub-icons respectively corresponding to the core and the penumbra.

When a type of an object is a brain of a dementia patient, image processing functions include segmentation of white matter hyper intensity (WMHI) (leukoaraiosis), segmentation of hippocampus and ventricle, measurement of volume, and tracing. An icon may be acquired as a brain shape and may include sub-icons respectively corresponding to white matter, hippocampus, and ventricle.

Although a type of an object is a brain, a sub-icon configuring an icon and an image processing function may be changed according to whether the brain is a brain of a dementia patient or a brain of a cerebral infarction patient. Therefore, a type of an object including a medical history of the object may be considered in acquiring an icon.

When a type of an object is a breast of a breast cancer patient, image processing functions include segmentation and selection of cancer and perfusion analysis. An icon may be acquired as a breast shape and may include a sub-icon corresponding to a cancer tissue.

As described above, an icon is generated in a shape of an object, and each sub-icon included in the icon may correspond to at least one image processing function associated with an anatomical region of a corresponding object.

According to another exemplary embodiment, an icon is generated in a shape of an object that is imaged. The icon may include sub-icons that correspond to internal or external regions or components of imaged object. Each sub-icon included in the icon may be configured to receive input or display a selectable menu item to perform one or more image processing functions to the region associated with the sub-icon. The display of the sub-icon may be updated to reflect the image processing that is performed to the region associated with the sub-icon.

Figure 11:
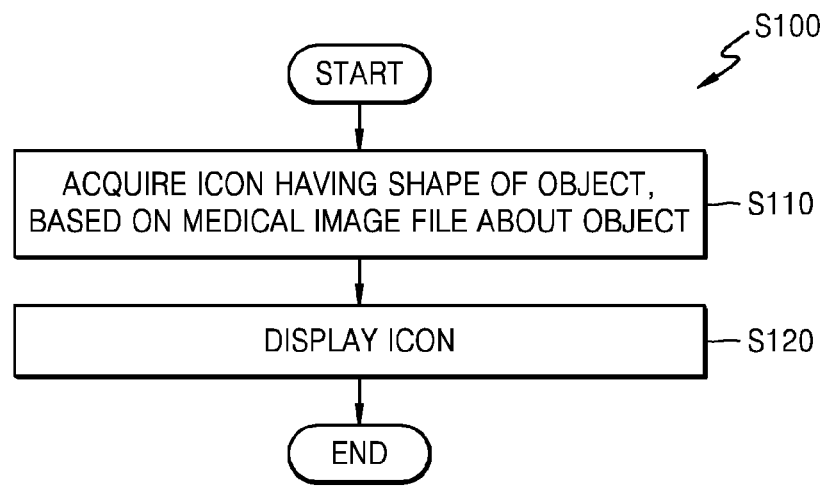
FIG. 11 is a flowchart illustrating a medical image processing method according to an exemplary embodiment.

FIG. 11 is a flowchart illustrating a medical image processing method according to an exemplary embodiment.

Referring to FIG. 11, in operation S110, an icon is acquired in a shape of an object, based on a medical image file about the object. In operation S120, an icon is displayed. The icon includes at least one sub-icon, which corresponds to an anatomical region of the object and corresponds to at least one image processing function associated with the corresponding anatomical region.

The medical image processing method S100 of FIG. 11 may be performed by the medical image processing apparatus 100 of FIG. 1. Each operation of the medical image processing method S100 may be performed in the above-described scheme.

Figure 12:
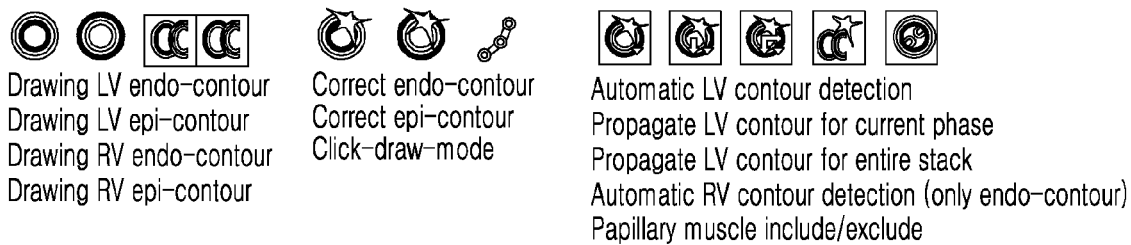
FIG. 12 is an example of a case in which an image processing function corresponds to each icon.

FIG. 12 is an example of a case in which an image processing function corresponds to each icon.

Referring to FIG. 12, when an object is a heart, a number of icons are displayed, and each of the icons corresponds to one image processing function. For example, when a user desires to perform a function of drawing an LV endo-contour, the user may find and select an icon, providing a corresponding image processing function, from among a number of icons. In order for the user to perform a desired image processing function, the user must already know the function of each image processing icon, thus causing the user inconvenience.

On the other hand, according to some exemplary embodiments, a number of individual icons illustrated in FIG. 12 may be replaced with one icon including at least one sub-icon that are configured to perform image processing functions. Thus, the number of displayed icons is reduced and the user can intuitively select an icon or a sub-icon. Since a corresponding image processing function is performed according to a sub-icon selecting scheme, medical image processing becomes convenient for a user. Therefore, according to some exemplary embodiments, a medical image processing apparatus and method which display an intuitive icon improve the experience and convenience of performing medical image processing.

The above-described exemplary embodiments may be written as computer programs and may be implemented in general-use digital computers that execute the programs using a computer readable recording medium.

Examples of the computer readable recording medium include magnetic storage media (e.g., ROM, floppy disks, hard disks, etc.) and optical recording media (e.g., CD-ROMs, or DVDs).

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A medical image processing apparatus comprising:
a display; and
at least one processor configured to:
identify a type of an object based on information in a medical image file of the object,
select an icon corresponding to the identified type of the object among at least one pre-stored icon, wherein the selected icon has a shape related to the object and comprises one or more sub-icons, each of the one or more sub-icons corresponds to a different anatomical region of the object,
control the display to display the selected icon,
receive a first selection operation selecting one sub-icon from the one or more sub-icons by a first sub-icon selecting scheme among a plurality of sub-icon selecting schemes, and
change a state of the sub-icon selected by the first selection operation, wherein the changed state of the sub-icon is selected based on the first sub-icon selecting scheme of the first selection operation and an image processing function corresponding to the first sub-icon selecting scheme, among a plurality of image processing functions, and visually presents the image processing function corresponding to the first selection operation,
wherein each of the plurality of sub-icon selecting schemes corresponds to a different image processing function, and corresponds to a different changed state of the one or more sub-icons.

2. The medical image processing apparatus of claim 1, wherein in response to the one sub-icon being selected by the first selection operation, the at least one processor controls the display to display a shortcut menu that provides the plurality of image processing functions corresponding to the selected sub-icon.

3. The medical image processing apparatus of claim 2, wherein in response to one image processing function from among the plurality of image processing functions displayed in the shortcut menu being selected by a user, the at least one processor performs an image processing on the medical image file by using the selected image processing function.

4. The medical image processing apparatus of claim 3, wherein the plurality of image processing functions displayed in the shortcut menu are selected by the user or selected according to a frequency of use.

5. The medical image processing apparatus of claim 1, wherein in response to the one sub-icon being selected by the first selection operation, the at least one processor performs an image processing on the medical image file by using the image processing function corresponding to the first selection operation.

6. The medical image processing apparatus of claim 1, wherein a correspondence relationship between the plurality of sub-icon selecting schemes and the plurality of image processing functions is selected by a user.

7. The medical image processing apparatus of claim 1, further comprising an input device configured to receive the first selection operation,
wherein, based on the first selection operation, the one sub-icon is selected from among the one or more sub-icons, and the image processing function is selected from among the plurality of image processing functions.

8. The medical image processing apparatus of claim 1, wherein the at least one processor selects the icon and determines the plurality of image processing functions based on the information about the object included in a header of the medical image file.

9. A medical image processing method comprising:
identifying, by at least one processor, a type of an object based on information in a medical image file of the object;
selecting, by the at least one processor, an icon corresponding to the identified type of the object among at least one pre-stored icon, wherein the selected icon has a shape related to the object and comprises one or more sub-icons, each of the one or more sub-icons corresponds to a different anatomical region of the object;
controlling, by the at least one processor, a display to display the selected icon;
receiving, by the at least one processor, a first selection operation selecting one sub-icon from the one or more sub-icons by a first sub-icon selecting scheme among a plurality of sub-icon selecting schemes; and
changing, by the at least one processor, a state of the sub-icon selected by the first selection operation, wherein the changed state of the sub-icon is selected based on the first sub-icon selecting scheme of the first selection operation and an image processing function corresponding to the first sub-icon selecting scheme, among a plurality of image processing functions, and visually presents the image processing function corresponding to the first selection operation,
wherein each of the plurality of sub-icon selecting schemes corresponds to a different image processing function, and corresponds to a different changed state of the one or more sub-icons.

10. The medical image processing method of claim 9, further comprising:
in response to the one sub-icon being selected by the first selection operation, controlling, by the at least one processor, the display to display a shortcut menu that provides the plurality of image processing functions corresponding to the selected sub-icon.

11. The medical image processing method of claim 10, further comprising:
in response to one image processing function from among the plurality of image processing functions displayed in the shortcut menu being selected by a user, performing, by the at least one processor, an image processing by using the selected image processing function.

12. The medical image processing method of claim 11, wherein the plurality of image processing functions displayed in the shortcut menu are selected by the user or are selected according to a frequency of use.

13. The medical image processing method of claim 9, further comprising:
in response to the one sub-icon being selected by the first selection operation, performing, by the at least one processor, an image processing on the medical image file by using the image processing function corresponding to the first selection operation.

14. The medical image processing method of claim 9, wherein a correspondence relationship between the plurality of sub-icon selecting schemes and the plurality of image processing functions is selected by a user.

15. The medical image processing method of claim 9, further comprising:

in response to the first selection operation, the one sub-icon is selected from among the one or more sub-icons, and the image processing function is selected from among the plurality of image processing functions.

16. A non-transitory computer program product comprising a computer readable storage medium having a computer readable program stored therein, wherein the computer readable program, when executed on a computing device, causes the computing device to execute the medical image processing method of claim 9.

17. An image processing method comprising:

acquiring, by at least one processor, information from an image file of an imaged object;

selecting, by the at least one processor, an icon corresponding to the imaged object based on the information among at least one pre-stored icon, wherein the selected icon comprises one or more sub-icons that respectively correspond to different regions of the imaged object;

controlling, by the at least one processor, a display to display the selected icon;

receiving, by the at least one processor, a first selection operation selecting one sub-icon from the one or more sub-icons by a first sub-icon selecting scheme among a plurality of sub-icon-selecting schemes; and changing, by the at least one processor, a state of the sub-icon selected by the first selection operation, wherein the changed state of the sub-icon is selected based on the first sub-icon selecting scheme of the first selection operation and an image processing function corresponding to the first sub-icon selecting scheme, among a plurality of image processing functions, and visually presents the image processing function corresponding to the first selection operation, wherein each of the plurality of sub-icon selecting schemes corresponds to a different image processing function, and corresponds to a different changed state of the one or more sub-icons.

18. The image processing method of claim 17, wherein the selecting the icon comprises retrieving the icon from a memory based on the information.

19. The image processing method of claim 17, wherein the selected icon comprises a shape related to the imaged object.

20. The image processing method of claim 17, wherein each of the one or more sub-icons comprises a shape related to a corresponding region, among the regions of the imaged object.

21. The image processing method of claim 17, wherein the image file comprises a medical image file.

22. The medical image processing apparatus of claim 1, wherein the changed state of the sub-icon corresponds to a visual state identified by at least one selected from dots, lines, pattern, and color.

23. The medical image processing apparatus of claim 1, wherein the plurality of sub-icon selecting schemes comprise at least one selected from a click, a left click, a right click, a double-click, a left double-click, a right double-click, a touch, a long tap, and a drag.

24. The medical image processing method of claim 9, wherein the changed state of the sub-icon corresponds to a visual state identified by at least one selected from dots, lines, pattern, and color.

25. The medical image processing method of claim 9, wherein the plurality of sub-icon selecting schemes comprise at least one selected from a click, a left click, a right click, a double-click, a left double-click, a right double-click, a touch, a long tap, and a drag.

* * * * *